United States Patent
Geisler et al.

Patent Number: 6,057,270
Date of Patent: May 2, 2000

[54] SUBSTITUTED PYRAZOLYL-PYRAZOLE DERIVATIVES, AND THEIR USE AS AGENTS WITH HERBICIDAL ACTION

[75] Inventors: Jens Geisler; Helga Franke; Uwe Hartfiel; Michael Ganzer; Jürgen Bohner, all of Berlin, Germany; Richard Rees, Pensacola, Fla.

[73] Assignee: Hoechst Schering AgrEvo GmbH, Berlin, Germany

[21] Appl. No.: 09/348,907

[22] Filed: Jul. 7, 1999

Related U.S. Application Data

[62] Division of application No. 09/148,383, Sep. 4, 1998, which is a division of application No. 08/809,391, filed as application No. PCT/EP95/03732, Sep. 21, 1995, Pat. No. 5,840,912.

[30] Foreign Application Priority Data

Sep. 22, 1994 [DE] Germany .................. 44 35 373

[51] Int. Cl.⁷ .................. A01N 43/56; C07D 231/38
[52] U.S. Cl. .................. 504/282; 504/237; 544/235; 548/365.4
[58] Field of Search .................. 548/365.4; 544/235; 504/282

[56] References Cited

FOREIGN PATENT DOCUMENTS 2146852   4/1994   Canada .

WO 94/08999   4/1994   WIPO .

OTHER PUBLICATIONS

Ramdani et al, Chemical Abstracts, vol. 95, No. 132840, 1981.

Primary Examiner—Robert W. Ramsuer
Attorney, Agent, or Firm—Frommer Lawerence & Haug LLP

[57] ABSTRACT

The invention relates to new substituted pyrazol derivatives of general formula (I) in which: $R^1$, $R^2$, $R^3$, $R^4$, $R^5$ and $R^6$ have the meanings given in the description, agents with herbicidal action containing at least one compound of formula (I), and their use as herbicides.

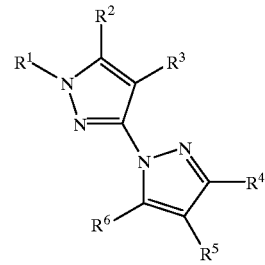

(I)

7 Claims, No Drawings

SUBSTITUTED PYRAZOLYL-PYRAZOLE DERIVATIVES, AND THEIR USE AS AGENTS WITH HERBICIDAL ACTION

This application is a divisional of application U.S. Ser. No. 09/148,383, filed on Sep. 4, 1998, now allowed, which in turn is a divisional application of U.S. Ser. No. 08/809,391, filed on Apr. 22, 1997, now U.S. Pat. No. 5,840,912, which is a national phase application filed 35 U.S.C. 371 of international application PCT/EP95/0732 which has an international filing date of Sep. 21, 1995.

The invention concerns new substituted pyrazolyl-pyrazole derivatives, their preparation as well as intermediate products for their preparation, and their use as agents with herbicidal action.

It is already known that pyrazoles possess herbicidal properties (WO 9408999). It frequently occurs however that the herbicidal action of the known compounds is not sufficient or selectivity problems occur with the relevant herbicidal action in main agricultural crops.

The problem of the present invention is to prepare new substituted pyrazole derivatives which do not exhibit these disadvantages and whose biological properties are superior to those of the currently known compounds.

It has now been found that substituted pyrazole derivatives of the general formula (I) have a superior herbicidal action:

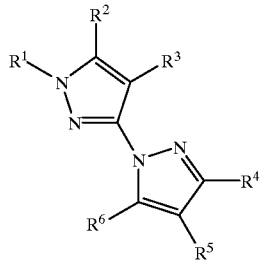

in which $R^1 = C_1-C_4$ alkyl, $R^2 = C_1-C_4$ alkyl, $C_1-C_4$ alkylthio, $C_1-C_4$ alkoxy; or $C_1-C_4$ alkyl, $C_1-C_4$, alkylthio, $C_1-C_4$ alkoxy all substituted one or more times with halogen, $R^1$ and $R^2$ together form the group —$(CH_2)_m$—, $R^3$ = hydrogen or halogen, $R^4$ = hydrogen or $C_1-C_4$ alkyl, $R^5$ = hydrogen, nitro, cyano or the groups —$COOR^7$,

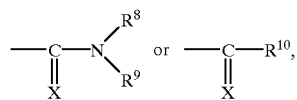

$R^6 =$

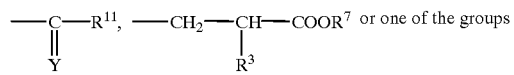

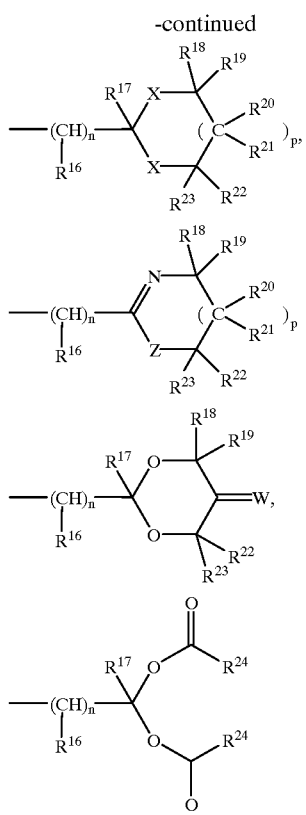

$R^7$, $R^8$ and $R^9$, independent of one another, are hydrogen or $C_1-C_4$ alkyl, $R^8$ and $R^9$, together with the adjacent nitrogen atom, form a 5-membered or 6-membered saturated heterocyclic ring, $R^{10}$ = hydrogen, $C_1-C_4$ alkyl, or a $C_1-C_4$ alkyl substituted one or more times by halogen, $R^{11}$ = hydrogen, $C_1-C_8$ alkyl, $C_3-C_6$ cycloalkyl, $C_2-C_6$ alkenyl, $C_3-C_6$ alkynyl; or $C_1-C_6$ alkyl, $C_3-C_8$ cycloalkyl, $C_2-C_6$ alkenyl, $C_3-C_6$ alkynyl all substituted similarly or differently one or more times by halogen, hydroxy or $C_1-C_4$ alkoxy; or $C_2-C_8$ alkyl, $C_3-C_6$ cycloalkyl, $C_3-C_8$ alkenyl, $C_3-C_6$ alkynyl all interrupted one or more times by oxygen; or the group $OR^{12}$, $R^{12}$ = hydrogen, $C_1-C_6$ alkyl, $C_3-C_6$ cycloalkyl, $C_2-C_6$ alkenyl, $C_3-C_6$ alkynyl; $C_1-C_6$ alkyl substituted similarly or differently one or more times by halogen, hydroxy or $C_1-C_4$ alkoxycarbonyl, $C_1-C_4$ alkyl or $C_1-C_4$ alkoxy, Y = oxygen, sulphur, —N—$OR^{13}$ and

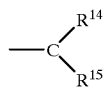

$R^{13}$ = hydrogen, $C_1-C_6$ alkyl, $C_3-C_6$ cycloalkyl, $C_2-C_6$ alkenyl, $C_3-C_6$ alkynyl; $C_1-C_6$ alkyl, $C_3-C_6$ cycloalkyl, $C_2-C_6$ alkenyl, $C_3-C_6$ alkynyl all substituted similarly or differently one or more times by halogen, cyano, hydroxy or $C_1-C_4$ alkoxy; $C_2-C_8$ alkyl, $C_3-C_6$ cycloalkyl, $C_3-C_8$ alkenyl, $C_3-C_8$ alkynyl all interrupted one or more times by oxygen; $C_1-C_4$ alkoxycarbonyl-$C_1$–$C_4$ alkyl, which can optionally be substituted by halogen atoms; $C_1$–$C_4$ alkoxycarbonyl-$C_2$–$C_4$ alkenyl, which can optionally be substituted by halogen atoms; $C_1$–$C_4$ alkoxycarbonyl, $R^{14}$ and $R^{15}$, independent of one another, are hydrogen, halogen, cyano, carboxyl, formyl, $C_1$–$C_6$ alkyl, $C_3$–$C_6$ cycloalkyl, $C_2$–$C_6$ alkenyl, $C_3$–$C_6$ alkynyl; $C_1$–$C_6$ alkyl, $C_3$–$C_6$ cycloalkyl, $C_2$–$C_6$ alkenyl, $C_3$–$C_6$ alkynyl all substituted similarly or differently one or more times by halogen, cyano, hydroxy or $C_1$–$C_4$ alkoxy; $C_2$–$C_8$ alkyl, $C_3$–$C_8$ cycloalkyl, $C_3$–$C_8$ alkenyl, $C_3$–$C_8$ alkynyl all interrupted one or more times by oxygen; $C_1$–$C_4$ alkoxycarbonyl-$C_2$–$C_4$ alkyl, which can optionally be substituted by halogen atoms; $C_1$–$C_4$ alkoxycarbonyl-$C_2$–$C_4$ alkenyl, which can optionally be substituted by halogen atoms; $C_1$–$C_4$ alkoxycarbonyl, $C_1$–$C_4$ alkoxy or $C_1$–$C_4$ alkylthio, $R^{14}$ and $R^{15}$ together with the carbon atom form a saturated carbocyclic $C_3$–$C_6$ ring which can be interrupted one or more times by oxygen or sulphur, $R^{16}$=hydrogen or $C_1$–$C_4$ alkyl, $R^{17}$=hydrogen, $C_1$–$C_4$ alkyl or halogen-$C_1$–$C_4$ alkyl, $R^{18}$, $R^{19}$, $R^{20}$, $R^{21}$, $R^{22}$ and $R^{23}$, independent if one another, are hydrogen, halogen, $C_1$–$C_4$ alkyl, $C_2$–$C_4$ alkenyl or $C_3$–$C_4$ alkynyl; $C_1$–$C_4$ alkyl, $C_2$–$C_4$ alkenyl, $C_3$–$C_4$ alkynyl, carboxyl or $C_1$–$C_4$ alkoxycarbonyl all substituted similarly or differently one or more times by halogen, cyano, nitro, hydroxy or by $C_1$–$C_4$ alkoxy, $R^{24}$=$C_1$–$C_4$ alkyl, or $C_1$–$C_4$ alkyl substituted one or more times by halogen, m=3 or 4, n=0, 1, 2 or 3, p=0 or 1, X=oxygen or sulphur, Z=oxygen, sulphur or N—$R^{25}$, $R^{25}$=hydrogen or $C_1$–$C_4$ alkyl, W=oxygen, sulphur or carbon.

The term "halogen" includes fluorine, chlorine and iodine.

The term "alkyl", "alkylene" and "alkynyl" implies that the carbon chain can be branched or unbranched.

The compounds of formula (I) which are preferred are those wherein:

$R^1$=methyl, $R^2$=methylthio or difluormethoxy, $R^1$ and $R^2$ together form the group —$(CH_2)_4$—, $R^3$=hydrogen, chlorine or bromine, $R^4$=hydrogen, $R^5$=hydrogen, nitro, cyano or the groups —$COOR^7$ or —$CXR^{10}$,

R=

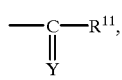

or one of the groups

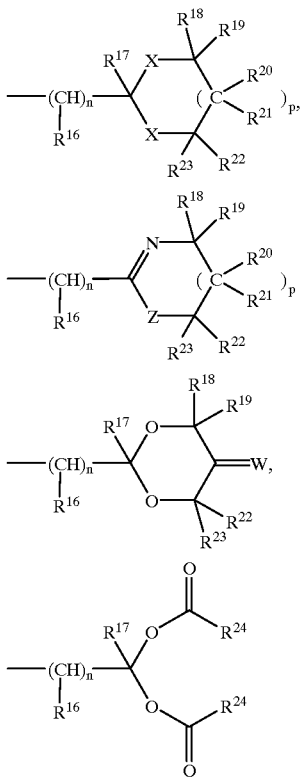

$R^7$=hydrogen or $C_1$–$C_4$ alkyl, $R^{10}$=hydrogen, $C_1$–$C_4$ alkyl, or a $C_1$–$C_4$ alkyl substituted one or more times by halogen, $R^{11}$=hydrogen, $C_1$–$C_6$ alkyl or the group —$OR^{12}$, $R^{12}$=$C_1$–$C_6$ alkyl, $C_3$–$C_6$ cycloalkyl, $C_2$–$C_6$ alkenyl, $C_3$–$C_6$ alkynyl; a $C_1$–$C_6$ alkyl substituted similarly or differently one or more times by halogen, hydroxy or $C_1$–$C_4$ alkoxy, Y=oxygen, sulphur, —N—$OR^{13}$ and

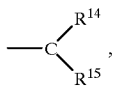

$R^{13}$=hydrogen, $C_1$–$C_6$ alkyl, $C_3$–$C_6$ cycloalkyl, $C_2$–$C_6$ alkenyl, $C_3$–$C_6$ alkynyl; $C_2$–$C_8$ alkyl, $C_3$–$C_8$ cycloalkyl, $C_3$–$C_8$ alkenyl, $C_3$–$C_8$ alkynyl all interrupted one or more times by oxygen; $C_1$–$C_4$ alkoxycarbonyl-$C_1$–$C_4$ alkyl, which can optionally be substituted by halogen atoms; $C_1$–$C_4$ alkoxycarbonyl-$C_2$–$C_4$ alkenyl, which can optionally be substituted by halogen atoms; $C_1$–$C_4$ alkoxycarbonyl, $R^{14}$ and $R^{15}$, independent of one another, are hydrogen, halogen, cyano, carboxyl, formyl, $C_1$–$C_6$ alkyl, $C_3$–$C_6$ cycloalkyl, $C_2$–$C_6$ alkenyl, $C_3$–$C_6$ alkynyl; $C_1$–$C_4$ alkoxycarbonyl-$C_1$–$C_4$ alkyl, which can optionally be substituted by halogen atoms; $C_1$–$C_4$ alkoxycarbonyl, $C_1$–$C_4$ alkoxy or $C_1$–$C_4$ alkylthio, $R^{16}$=hydrogen or $C_1$–$C_4$ alkyl, $R^{17}$=hydrogen, $C_1$–$C_4$ alkyl or halogen-$C_1$–$C_4$ alkyl, $R^{18}$, $R^{19}$, $R^{20}$, $R^{21}$, $R^{22}$ and $R^{23}$, independent if one another, are hydrogen, halogen, $C_1$–$C_4$ alkyl, $C_2$–$C_4$ alkenyl or $C_3$–$C_4$ alkynyl; $C_1$–$C_4$ alkyl, $C_2$–$C_4$ alkenyl, $C_3$–$C_4$ alkynyl, carboxyl or $C_1$–$C_4$ alkoxycarbonyl all substituted similarly or differently one or more times by halogen, cyano, nitro, hydroxy or by $C_1$–$C_4$ alkoxy, $R^{24}$=$C_1$–$C_4$ alkyl, or $C_1$–$C_4$ alkyl substituted one or more times by halogen, m=3 or 4, n=0, 1, 2 or 3, p=0 or 1, X=oxygen or sulphur, Z=oxygen, sulphur or N—$R^{25}$, $R^{25}$=hydrogen or $C_1$–$C_4$ alkyl, W=oxygen, sulphur or carbon.

Especially preferred are such compounds of formula (I) in which $R^1$=methyl, $R^2$=difluormethoxy, $R^1$ and $R^2$ together form the group —$(CH_2)_4$—, $R^3$=chlorine, $R^4$=hydrogen, $R^5$=nitro or cyano, $R^6$=

$$-\underset{\underset{Y}{\|}}{C}-R^{11},$$

or the group

[structure with $R^{16}$, $R^{17}$, $R^{18}$, $R^{19}$, $R^{20}$, $R^{21}$, $R^{22}$, $R^{23}$, X, $(CH)_n$, $(C)_p$]

$R^{11}$=hydrogen or the group —$OR^{12}$, $R^{12}$=$C_1$–$C_6$ alkyl,

Y=oxygen, —N—$OR^{13}$ and $$C\diagdown\!\!\!\!{}^{R^{14}}_{R^{15}},$$

$R^{13}$=$C_1$–$C_6$ alkyl, $R^{14}$ and $R^{15}$, independent of one another, are hydrogen, halogen or $C_1$–$C_4$ alkoxy, $R^{16}$=hydrogen, $R^{17}$=hydrogen, $R^{18}$, $R^{19}$, $R^{20}$, $R^{21}$, $R^{22}$ and $R^{23}$, independent if one another, are hydrogen, halogen, $C_1$–$C_4$ alkyl, $C_1$–$C_4$-alkoxycarbonyl-$C_1$–$C_4$-alkyl, or $C_1$–$C_4$-haloalkyl, n=0, p=0 or 1, and X=oxygen.

The compounds of the general formula (I) according to the invention can be prepared as follows:

A) a compound of the general formula (II)

$$\text{II}$$

[structure of formula II with $R^1$, $R^2$, $R^3$, —NHNH$_2$]

in which $R^1$, $R^2$ and $R^3$ have the meanings given in the general formula (I), is reacted with a compound of the general formula (III)

$$\text{III}$$

[structure of formula III with $R^5$, $R^6$, B]

in which $R^5$ stands for the group —COOR$^7$ or the group $$-\underset{\underset{}{\|}}{\overset{X}{C}}-N\diagdown\!\!\!\!{}^{R^8}_{R^9}$$

whereby $R^7$, $R^8$ and $R^9$ have the meaning given in the general formula (I) and X stands for oxygen, $R^6$ has the meaning given in the general formula (I) but contains no formyl groups and B stands for the group —OR$^{26}$ or $$N\diagdown\!\!\!\!{}^{R^{27}}_{R^{26}}$$

whereby $R^{26}$, $R^{27}$ and $R^{28}$ independent of one another mean $C_1$–$C_4$ alkyl, or B) in the case where $R^6$ stands for the formyl group, a compound of the general formula (Ia)

$$\text{Ia}$$

[structure of formula Ia with $R^1$, $R^2$, $R^3$, $R^4$, $R^5$, CH$_2$, A]

in which $R^1$, $R^2$, $R^3$, $R^4$ and $R^5$ have the meaning given in the general formula (I), and A stands for hydrogen, halogen, hydroxy, an alkyl- or aryl-sulphonyl group, is reacted with a suitable oxidising agent, or C) in the case where $R^6$ stands for the group —CYR$^{11}$, whereby $R^{11}$ has the meaning given in the general formula (I) and Y stands for oxygen, a compound of the general formula (Ib)

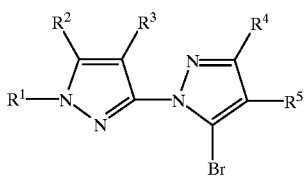

in which $R^1$, $R^2$, $R^3$, $R^4$ and $R^5$ have the meaning given in the general formula (1), is metallised with a suitable base and is then (reacted) with an acyl compound of the general formula IV or V

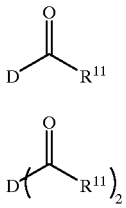

in which $R^{11}$ has the meaning given in the general formula (I)
and D stands for chlorine, bromine,

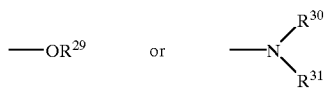

whereby $R^{29}$, $R^{30}$ and $R^{31}$ stand for $C_1$–$C_4$ alkyl. Should $R^{11}$ stand for hydrogen, then the
meaning of D is constrained to —$OR^{29}$ and to

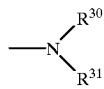

D) in the case where $R^6$ stands for the group

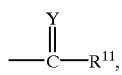

in which
$R^{11}$ has the meaning given in the general formula (I) and Y stands for sulphur, a compound of the general formula (Ic)

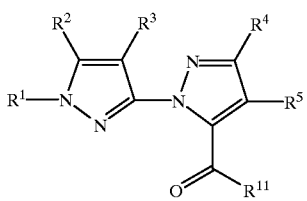

in which $R^1$, $R^2$, $R^3$, $R^4$, $R^5$ and $R^{11}$ have the meaning given in the general formula (I), is reacted with Lawessons reagent, or E) in the case where $R^6$ stands for the group

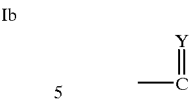

in which $R^{11}$ has the meaning given in the general formula (I) and Y stands for the group —N—$OR^{13}$, in which $R^{13}$ has the meaning given in the general formula (I), a compound of the general formula (Ic)

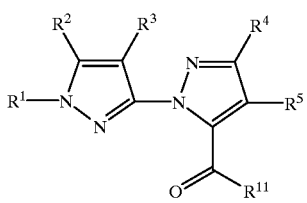

in which $R^1$, $R^2$, $R^3$, $R^4$, $R^5$ and $R^{11}$ have the meaning given in the general formula (I), is reacted with a compound of the general formula VI

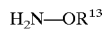

in which $R^{13}$ has the meaning given in the general formula (I), or

F) in the case where $R^6$ stands for the group

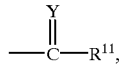

in which $R^{11}$ has the meaning given in the general formula (I) and Y stands for

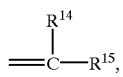

whereby $R^{14}$ and $R^{15}$ have the meaning given in the general formula (I), a compound of the general formula (Ic)

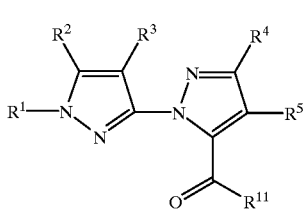

in which $R^1$, $R^2$, $R^3$, $R^4$, $R^5$ and $R^{11}$ have the meaning given in the general formula (I), is reacted with a compound of the general formula VIl or VIII

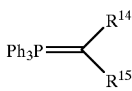

-continued

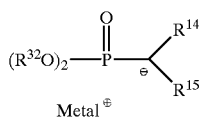

VIII in which $R^{14}$ and $R^{15}$ have the meaning given in the general formula (I) and where $R^{32}$ stands for $C_1$–$C_4$ alkyl, or G) in the case where $R^6$ stands for halogen, a compound of the general formula (Id)

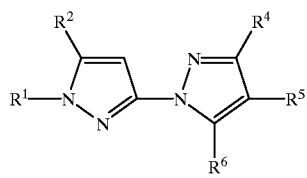

Id in which $R^1$, $R^2$, $R^3$, $R^4$, $R^5$ and $R^6$ have the meaning given in the general formula (I), is reacted with a suitable halogenating agent, or H) in the case where $R^6$ stands for one of the groups

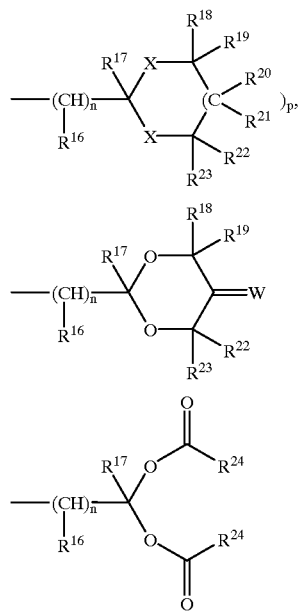

in which $R^{16}$, $R^{17}$, $R^{18}$, $R^{19}$, $R^{20}$, $R^{21}$, $R^{22}$, $R^{23}$, $R^{24}$, n, p and W have the meaning given in the general formula (I), a compound of the general formula (Ie)

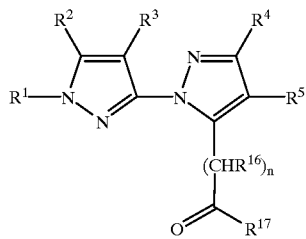

Ie in which $R^1$, $R^2$, $R^3$, $R^4$, $R^5$, $R^{16}$, $R^{17}$ and n have the meaning given in the general formula (I), is reacted with a compound of the general formula IX, X or XI

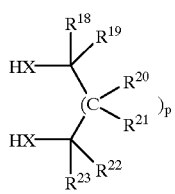

IX

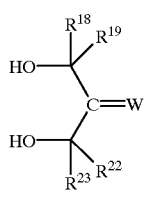

X

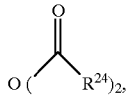

XI in which $R^{18}$, $R^{19}$, $R^{20}$, $R^{21}$, $R^{22}$, $R^{23}$, $R^{24,}$ p and W have the meaning given in the general formula (I), or I) in the case where $R^6$ stands for the group

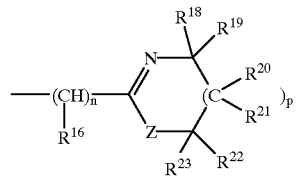

in which $R^{16}$, $R^{18}$, $R^{19}$, $R^{20}$, $R^{21}$, $R^{22}$, $R^{23}$, n and p have the meaning given in the general formula (I), a compound of the general formula (If)

If

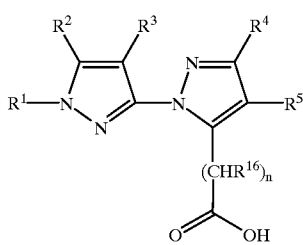

in which $R^1$, $R^2$, $R^3$, $R^4$, $R^5$, $R^{16}$ and n have the meaning given in the general formula (I), is reacted with a compound of the general formula XII

XII

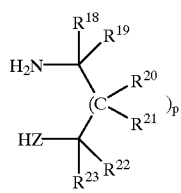

where $R^{18}$, $R^{19}$, $R^{20}$, $R^{21}$, $R^{22}$, $R^{23}$, Z and p have the meaning given in the general formula (I), or J) a compound of the general formula (Ig)

Ig

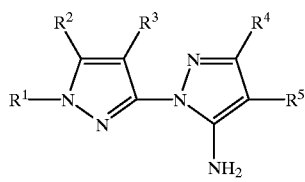

in which $R^1$, $R^2$, $R^3$, $R^4$ and $R^5$ have the meaning given in the general formula (I), is firstly diazotised to give a compound of the general formula (Ih)

Ih

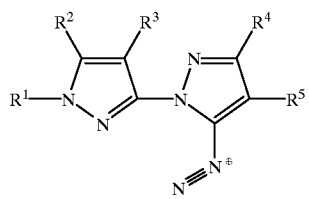

in which $R^1$, $R^2$, $R^3$, $R^4$ and $R^5$ have the meaning given in the general formula (I), and is then reacted with a Michael-acceptor of the general formula XIII

XIII

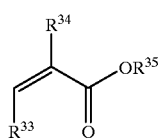

in which $R^{33}$ and $R^{34}$, independent of one another, mean hydrogen, $C_1$–$C_4$ alkyl or halogen, and $R^{35}$ means $C_1$–$C_4$, alkyl, or K) a compound of the general formula (If) is esterified with an alcohol of the general formula XIV $R^{12}$—OH       XIV in which $R^{12}$ has the meaning given in the general formula (I).

The compounds of the general formula (I) according to the invention, in which $R^5$ stands for the groups —$COOR^7$ or —$CXNR^8R^9$, can be prepared by the process described by Bisagni et al in Tetrahedron, 29, 435 (1973).

The oxidation according to process variant B) may be carried out by the processes such as are described for example in Houben-Wehl, Vol VII, 1, page 135 et seq (1954) or in Vol E3, page 231 et seq (1983). The compounds of general formula (Ia) used as starting materials are known (WO 94 08 999).

The process variant C) is carried out effectively by reacting the starting material of formula (Ib) in a suitable solvent at a temperature from −100 to +40° C. with a suitable base to give a compound of the general formula (Ii)

Ii

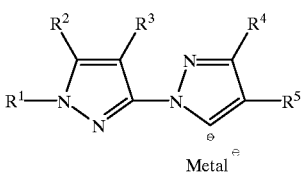

in which $R^1$, $R^2$, $R^3$, $R^4$ and $R^5$ have the meaning given in the general formula (I) and metal$^\oplus$ stands for a metal cation such as for example lithium, sodium or potassium. The intermediate compound of the formula (Ii) is reacted directly, ie, without any further processing, with a compound of formula IV or V at a temperature from −100 to +100° C.

Ethers, such as for example diethyl ether, tetrahydrofuran or 1,4-dioxane, may be cited as suitable solvents.

Butyl lithium, lithium diisopropylamide, sodium hydride or potassium tert. butylate may be cited as bases.

The compounds of the general formula (Ib) used as starting materials are known. Their preparation is described in WO 94 08 999.

The process variant D) can be carried out for example according to the methods described in Bull Soc Chim Belg, 87, 223, 229, 299 or 525, (1978).

The formation of oxime-ether in process variant E) can be carried out according to known processes such as are described for example in Houben-Wehl, Vol X4, page 55 et seq (1968).

The compounds involved in process variant F) can be prepared by the methods described in "Advanced Organic Chemistry", 1985, page 864 et seq and in the literature cited therein.

Sulphuryl chloride, sodium hypochlorite, N-chlorosuccinimide, N-bromosuccinimide, chlorine or bromine are examples of halogenating agents which may be used.

The acetals or ketals may be prepared by the methods described by T W Greene in "Protective Groups in Organic Synthesis", 1980, page 116 et seq.

The compounds according to the invention in accordance with process variant I) can be prepared by the process described by A I Meyers in J Am Chem Soc, 92, 6644 (1970).

The compounds according to the process variant J) can be prepared according to the process cited in U.S. Pat. No. 5,250,504.

The esterifications according to the last process stage are known per se and they can be carried out according to the usual methods, such as for example those described in Houben-Wehl, Vol E5, page 659 et seq (1985).

The preparation can be carried out with or without solvents whereby if necessary such solvents or diluents which are inert with regard to the respective reactants may be used. Examples of such solvents or diluents respectively are aliphatic and aromatic hydrocarbons each of which may optionally be chlorinated, such as for example hexane, cyclohexane, petroleum ether, white spirit, benzene, toluene, xylene, methylene chloride, chloroform, carbon tetrachloride, ethylene chloride, trichloroethylene and chlorobenzene; ethers such as for example diethyl ether, methyl ethyl ether, methyl t-butyl ether, diisopropyl ether, dibutyl ether, dioxane and tetrohydrofuran; ketones such as for example acetone, methyl ethyl ketone, methylisopropyl ketone, methylisobutyl ketone; nitrites such as for example acetonitrile and propionitrile; alcohols such as for example methanol, ethanol, isopropanol, butanol, tert-butanol, tert-amyl alcohol and ethylene glycol; esters such as for example ethyl acetate and amyl acetate, acid amides such as for example dimethyl formamide and dimethyl acetamide, sulphoxides such as for example dimethyl sulphoxide, sulphones such as for example sulpholane, bases such as for example pyridine and triethylamine, carboxylic acids such as for example acetic acid, and mineral acids such as for example sulphuric acid and hydrochloric acid.

The usual procedures are used for working-up the compounds according to the invention. Purification is carried out by crystallisation or by column chromatography.

The compounds according to the invention are generally colourless or slightly yellow-coloured crystalline or viscous substances which for the most part are readily soluble in chlorinated hydrocarbons, such as for example methylene chloride or chloroform, ethers such as for example diethyl ether or tetrahydrofuran, alcohols such as for example methanol or ethanol, ketones such as for example acetone or butanone, amides such as for example dimethylformamide and also sulphoxides such as for example dimethyl sulphoxide.

The compounds according to the invention display good herbicidal action on broad-leaved weeds and grasses. Selective application is possible with various crops, for example rape, beet, soya beans, cotton, rice, maize, barley, wheat and other kinds of cereals. Individual compounds are also suitable as selective herbicides for beet, cotton, soya, maize and cereal. Furthermore the compounds can be used for weed-killing during long-term cultivation such as for example in plantations for forestry, decorative wood, fruit, wine, citrus, nuts, bananas, coffee, tea, rubber, oil-palm, cocoa, fruit berries and hops.

The compounds according to the invention can be used for example for the following plant species:

Dicotyledonous weeds of genus such as Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Sonchus, Solanum, Lamium, Veronica, Abutilon, Datura, Viola, Galeopsis, Papaver, Centaurea and Chrysanthemum; monocotyledonous weeds of genus such as Avena, Alopecurus, Echinochloa, Sataria, Panicum, Digitaria, Poa, Eleusine, Brachiaria, Lolium, Bromus, Cyperus, Elymus, Sagittaria, Monochoria, Fimbristylis, Eleocharis, lschaemum and Apera.

The applied amounts vary depending on the type of use and the stage of growth between 0.001 and 5 kg/ha.

The active agents according to the invention can also be used as defoliants, desiccants and weed-killing agents.

Enhancement of the intensity of action and the speed of action can be achieved for example by the use of additives which magnify the effect, such as organic solvents, wetting agents and oils. The use of such additives therefore optionally leads to a reduction in the dosage of the active material.

The active agents according to the invention or their mixtures are desirably applied in the form of preparations such as powders, spreading agents, granulates, solutions, emulsions or suspensions, with the addition of liquid and/or solid carriers or diluents respectively and optionally with bonding agents, wetting agents, emulsifying agents and/or dispersion aids.

Suitable liquid carriers are for example aliphatic and aromatic hydrocarbons such as benzene, toluene, xylene, cyclohexanone, isophorone, dimethyl sulphoxide, dimethyl formamide and also mineral oil fractions and vegetable oils.

Suitable solid carriers are minerals such as for example bentonite, silica gel, talc, kaolin, Attapulgit, chalk and vegetable products such as for example flour.

Examples of surfactants are calcium lignin sulphonate, polyethylene alkylphenyl ether, naphthalene sulphonic acids and their salts, phenol sulphonic acids and their salts, condensates of formaldehyde, fatty alcohol sulphates as well as substituted benzene sulphonic acids and their salts.

The amount of the respective active agent(s) in the various preparations can vary over a wide range. For example, the material contains about 10 to 90 weight % active agent, about 90 to 10 weight % liquid or solid carrier and optionally up to 20 weight % surfactant.

Application of the material can occur in the usual way, for example with water as the carrier in spraying amounts of about 100 to 1000 litre/ha. Application of the material in the so-called Low-Volume-Process and the Ultra-Low-Volume-Process is also possible as is its application in the form of so-called micro-granules.

The preparation of these mixtures can be carried out in a way known per se, for example by milling or mixing processes. If desired, preparations of the individual components can be mixed shortly before their use, as carried out in practice for example in the so-called tank-mix process.

The following Examples describe the preparation of the compounds according to the invention.

EXAMPLE 1

(Process B)

1(4-chlor-5-difluormethoxy-1-methyl-3-pyrazolyl)-5-formyl-4-pyrazol-carbonitrile 29 g (9.6 mmol) 1-(4-chlor-5-difluormethoxy-1-methyl-3-pyrazolyl)-5-hydroxymethyl-4-pyrazol-carbonitrile is added to 30 ml dichloromethane and 15.2 g pyridinium chlorochromate on aluminium oxide is then added. Stirring continues for 1 hour at room temperature and then the reaction mixture is vacuum filtered through Celite and purified by means of column chromatography using hexane/ethyl acetate.

Yield: 1.8 g=62% of theory $n_D^{20}$=1.54066

EXAMPLE 2

(Process E)

(E/Z) 1-(4chlor-5-difluormethoxy-1-methyl-3-pyrazolyl)-5-methoxyiminomethyl-4-carbonitrile 0.46 g (1.5 mmol) 1-(4-chlor-5-difluormethoxy-1-methyl-3-pyrazolyl)-5-formyl-4-pyrazol-carbonitrile is added to 4 ml pyridine at room temperature and 0.25 g (3.0 mmol) O-methyl-hydroxylamine hydrochloride is added. The mixture is stirred for 2 hours at room temperature, poured into water and shaken with ethyl acetate. It is dried over magnesium sulphate and concentrated. Purification is by column chromatography using hexane/ethyl acetate.

Yield: 0.3 g=60% of theory

Freeze point: 95–98° C.

EXAMPLE 3
(Process F)

1-(4 chlor-5-difluormethoxy-1-methyl-3-pyrazolyl)-5-(2-methoxyvinyl)-4-pyrazol-carbonitrile 2.9 g (8.4 mmol) methoxymethylene-triphenylphosphonium chloride is added to 10 ml tetrahydrofuran and 5.6 ml (9.0 mmol) of a 1,6 molar solution of butyl lithium in hexane is slowly added dropwise at 0° C. The orange-coloured solution is stirred for another 30 minutes and then 1.0 g (3.3 mmol) 1-(4-chlor-5-difluormethoxy-1-methyl-3-pyrazolyl)-5-formyl-4-pyrazol-carbonitrile is slowly added dropwise. Stirring continues for 2 hours at room temperature. The reaction mixture is then added to water, shaken with ethyl acetate, dried over magnesium sulphate and concentrated. Purification is by column chromatography using a hexane/ethyl acetate mixture.

EXAMPLE 4
(Process H)

1-(4-chlor-5-difluormethoxy-1-methyl-3-pyrazolyl)-5-(1,3-dioxolan-2-yl)-4-pyrazol-carbonitrile 0.6 g (2.0 mmol) 1-(4-chlor-5-difluormethoxy-1-methyl-3pyrazolyl)-5-formyl-4-pyrazol-carbonitrile is dissolved in 30 ml toluene and 0.14 g (2.2 mmol) ethylene glycol and a catalytic amount of p-toluene sulphonic acid are added. The mixture is heated for 2 hours on the water-separator, the cooled solution is washed with sodium chloride solution, and it is then dried and concentrated.

Yield: 0.68 g=98% of theory

Freeze point: 70–72° C.

EXAMPLE 5
(Process H)

1-(4-chlor-5-difluormethoxy-1-methyl-3-pyrazolyl)-5-(1,1-diacetoxymethyl)pyrazol-4-carbonitrile 5 ml acetic anhydride is cooled to 0–5° C. and 2 drops boron trifluoride-etherate are added. Then 2.3 g (7.6 mmol) 1-(4-chlor-5-difluormethoxy-1-methyl-3-pyrazolyl)-5-formyl-4-pyrazol-carbonitrile is slowly added dropwise and stirring is continued for another 1.5 hours at room temperature. 9 ml of 10% sodium acetate solution is added, stirring is continued for 20 minutes at room temperature and then the mixture is shaken up with ethyl acetate. The combined ethyl acetate phases are washed with a solution of sodium hydrogen carbonate and sodium chloride, dried and concentrated. Purification is by column chromatography using a hexane/ethyl acetate mixture.

Yield: 2.5 g=80% of theory

Freeze point: 84–85° C.

EXAMPLE 6
(Process J)

2chlor-3-[1-(3-chlor-4,5,6,7-tetrahydropyrazolo-[1,5-a]-pyridin-2-yl)-4-cyan-5-pyrazolyl]-2-methyl-propionic acid ethyl ester 1.6 g (15.5 mmol) tert-butyl nitrite, 20 ml ethyl methacrylate and 1.52 g copper-ll-chloride is added to 20 ml acetonitrile and 2.62 g (10 mmol) 5-amino-1-(3-chlor-4,5,6,7-tetrahydropyrazolo-[1,5-a]-pyridin-2-yl)-4-pyrazol-carbonitrile is added in 3 portions. The mixture is stirred at room temperature for 20 hours, added to 50 ml 2N hydrochloric acid, extracted 3 times with dichloromethane, dried over magnesium sulphate and concentrated. Purification is by column chromatography using a hexane/ethyl acetate mixture.

Yield: 1.6 g=40% of theory $n_D^{20}$=1.54164

EXAMPLE 7
(Process K)

1-(3-chlor-4,5,6,7-tetrahydropyrazolo-[1,5-a]-pyridin-2-yl)-4-cyan-5-pyrazol-carboxylic-acid-isopropylester.

757 mg (2.7 mmol) of azodicarboxylic acid diethylester is added dropwise to 800 mg (2.7 mmol) 1-(3-chlor-4,5,6,7-tetrahydropyrazolo-[1,5-a]pyridin-2-yl)-4-cyan-5-pyrazol-carboxylic-acid. The mixture is stirred for 2 hours at this temperature, then concentrated and purified by column chromatography using SiO₂/hexane/ethyl acetate. The residue is recrystallised from diisopropyl ether.

Yield: 570 mg=62% of theory $n_D^{20}$=1.53942

The following compounds of formula (I) are prepared in an analogous fashion, wherein $R^4$ is just hydrogen.

| No. | $R^1$ | $R^2$ | $R^3$ | $R^5$ | $R^6$ | Freeze pt. [° C.] or $n_D$ (° C.) |
|---|---|---|---|---|---|---|
| 8 | $CH_3$ | $OCHF_2$ | Cl | CN | 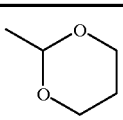 | 148–150 |
| 9 | $CH_3$ | $OCHF_2$ | Cl | CN | 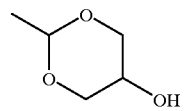 | viscous oil |

-continued
| No. | R¹ | R² | R³ | R⁵ | R⁶ | Freeze pt. [° C.] or $n_D$ (° C.) |
|---|---|---|---|---|---|---|
| 10 | CH₃ | OCHF₂ | Cl | CN | 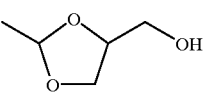 | viscous oil |
| 11 | CH₃ | OCHF₂ | Cl | CN | 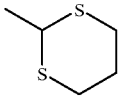 | 140–142 |
| 12 | CH₃ | OCHF₂ | Cl | CN | 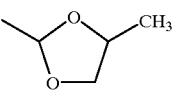 | viscous oil |
| 13 | CH₃ | OCHF₂ | Br | CN | 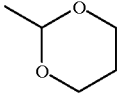 | 145 |
| 14 | —(CH₂)₄— | | Cl | CN | 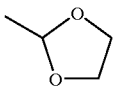 | 106–108 |
| 15 | —(CH₂)₄— | | Cl | CN | 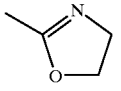 | |
| 16 | —(CH₂)₄— | | Br | CN | 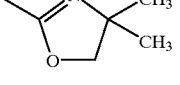 | |
| 17 | —(CH₂)₄— | | Cl | NO₂ | 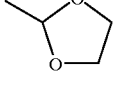 | |
| 18 | CH₃ | OCHF₂ | Cl | CN | 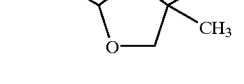 | |
| 19 | CH₃ | OCHF₂ | Cl | CN | 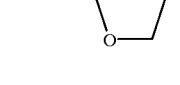 | |
| 20 | CH₃ | OCHF₂ | Cl | CN | 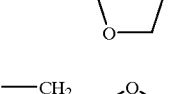 | |
| 21 | CH₃ | OCHF₂ | Cl | CN | 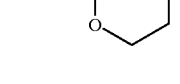 | |
| 22 | CH₃ | OCHF₂ | Br | CN | 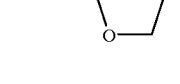 | |

-continued

| No. | $R^1$ | $R^2$ | $R^3$ | $R^5$ | $R^6$ | Freeze pt. [° C.] or $n_D$ (° C.) |
|---|---|---|---|---|---|---|
| 23 | $CH_3$ | $OCHF_2$ | Cl | $NO_2$ | —$CH_2$—(4,4-dimethyl-4,5-dihydrooxazol-2-yl) | |
| 24 | $CH_3$ | $OCHF_2$ | Cl | CN | —$CH_2$—$CH_2$—(1,3-dioxolan-2-yl) | |
| 25 | $CH_3$ | $OCHF_2$ | Cl | CN | —$CH_2$—$CH_2$—(1,3-dioxan-2-yl) | |
| 26 | —$(CH_2)_4$— | | Cl | CN | —$CH_2$—$CH_2$—(5-oxo-1,3-dioxan-2-yl) | |
| 27 | —$(CH_2)_4$— | | Cl | CN | —$CH_2$—(4-methoxymethyl-1,3-dioxolan-2-yl) | |
| 28 | —$(CH_2)_4$— | | Cl | CN | —$CH_2$—(4-methoxycarbonylmethyl-1,3-dioxolan-2-yl) | |
| 29 | —$(CH_2)_4$— | | Br | CN | —$CH_2$—(1,3-dioxan-2-yl) | |
| 30 | —$(CH_2)_4$— | | Br | $NO_2$ | (5,5-dimethyl-1,3-dioxan-2-yl) | |
| 31 | $CH_3$ | $OCHF_2$ | Cl | CN | (5-methylene-1,3-dioxan-2-yl) | 115–117 |
| 32 | $CH_3$ | $OCHF_2$ | Cl | CN | (1,3-oxathiolan-2-yl) | 1.5327 (20) |
| 33 | $CH_3$ | $OCHF_2$ | Cl | CN | (5-methoxy-1,3-dioxan-2-yl) | |
| 34 | $CH_3$ | $OCHF_2$ | Cl | CN | (4-methoxymethyl-1,3-dioxolan-2-yl) | 1.515 (20.1) |
| 35 | $CH_3$ | $OCHF_2$ | Cl | CN | (4-methoxycarbonylmethyl-1,3-dioxolan-2-yl) | |

-continued

| No. | R¹ | R² | R³ | R⁵ | R⁶ | Freeze pt. [° C.] or $n_D$ (° C.) |
|---|---|---|---|---|---|---|
| 36 | CH₃ | OCHF₂ | Cl | CN | —CH=CH—(1,3-dioxolan-2-yl) cis | |
| 37 | CH₃ | OCHF₂ | Cl | CN | —CH=CH—(1,3-dioxolan-2-yl) trans | |
| 38 | CH₃ | OCHF₂ | Cl | CN | —CO₂CH₃ | 131–132 |
| 39 | CH₃ | OCHF₂ | Br | CN | —CO₂C₂H₅ | 72 |
| 40 | CH₃ | OCHF₂ | Cl | NO₂ | —CO₂C₂H₅ | |
| 41 | CH₃ | OCHF₂ | Cl | CN | —CH=CH—CO₂C₂H₅ (t) | |
| 42 | CH₃ | OCHF₂ | Cl | CN | —CH=CH—CO₂CH₃ (t) | |
| 43 | —(CH₂)₄— | | Cl | CN | —CO₂CH₃ | 115–116 |
| 44 | —(CH₂)₄— | | Cl | CN | —CO₂C₂H₅ | 1.55882 (20) |
| 45 | —(CH₂)₄— | | Cl | CN | —CH₂CHCl—CO₂C₂H₅ | 1.54920 (20) |
| 46 | —(CH₂)₄— | | Cl | CN | —CO₂—CH₂CH₂CH₃ | 83–85 |
| 47 | —(CH₂)₄— | | Cl | CN | —CH=CH—CO₂C₂H₅ | 132–133 |
| 48 | CH₃ | OCHF₂ | Cl | CN | —CH=N—OC₂H₅ | |
| 49 | CH₃ | OCHF₂ | Cl | CN | —CH=N—OCH₂C≡CH | |
| 50 | CH₃ | OCHF₂ | Cl | CN | —CH=CCl₂ | |
| 51 | CH₃ | OCHF₂ | Br | CN | —CH=CBr₂ | |
| 52 | CH₃ | OCHF₂ | Cl | NO₂ | —CH=N—OCH₃ | 88–89 |
| 53 | CH₃ | OCHF₂ | Cl | CN | —OCH₃=N—CCH₃ | |
| 54 | CH₃ | OCHF₂ | Cl | CN | —CH=CH—CN | |
| 55 | —(CH₂)₄— | | Cl | CN | —CCH₃=CH—C₂H₅ | |
| 56 | —(CH₂)₄— | | Br | CN | —CCF₃=CH₂ | |
| 57 | —(CH₂)₄— | | Cl | NO₂ | —CH=CH—CCH₃=CH₂ | |
| 58 | CH₃ | OCHF₂ | Cl | CN | —CH=N—OCH₂—CH=CH₂ | 1.5344 (20) |
| 59 | CH₃ | OCHF₂ | Br | CN | —CH=N—OC₂H₅ | |
| 60 | CH₃ | OCHF₂ | Cl | CN | 4-methyl-1,3-dioxan-2-yl | 1.5372 (20) |
| 61 | CH₃ | OCHF₂ | Cl | NO₂ | —CH(OCOCH₃)₂ | |
| 62 | CH₃ | OCHF₂ | Cl | NO₂ | 1,3-dioxan-2-yl | 133–134 |
| 63 | CH₃ | OCHF₂ | Cl | NO₂ | 4-methyl-1,3-dioxan-2-yl | 127–128 |
| 64 | CH₃ | OCHF₂ | Cl | NO₂ | 4,6-dimethyl-1,3-dioxan-2-yl | 98 |
| 65 | CH₃ | OCHF₂ | Cl | NO₂ | 1,3-dioxolan-2-yl | 73–75 |

-continued
| No. | R¹ | R² | R³ | R⁵ | R⁶ | Freeze pt. [° C.] or $n_D$ (° C.) |
|---|---|---|---|---|---|---|
| 66 | CH₃ | OCHF₂ | Cl | NO₂ | 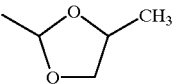 | 1.516 (20.2) |
| 67 | CH₃ | OCHF₂ | Cl | NO₂ | 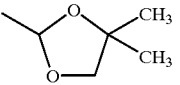 | |
| 68 | CH₃ | OCHF₂ | Br | NO₂ | 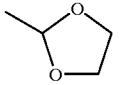 | |
| 69 | CH₃ | OCHF₂ | Cl | NO₂ | 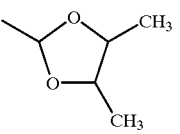 | |
| 70 | CH₃ | OCHF₂ | Cl | NO₂ | 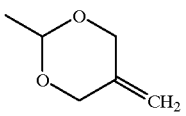 | |
| 71 | CH₃ | OCHF₂ | Cl | NO₂ | 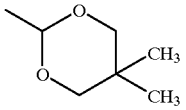 | 108 |
| 72 | CH₃ | OCHF₂ | Cl | NO₂ | 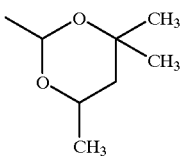 | |
| 73 | CH₃ | OCHF₂ | Cl | NO₂ | 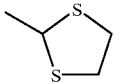 | |
| 74 | CH₃ | OCHF₂ | Cl | NO₂ | 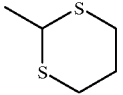 | |
| 75 | CH₃ | OCHF₂ | Cl | NO₂ | 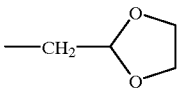 | |
| 76 | CH₃ | OCHF₂ | Cl | NO₂ | 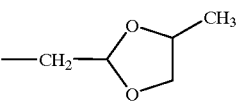 | |
| 77 | CH3 | OCHF₂ | Cl | NO₂ | 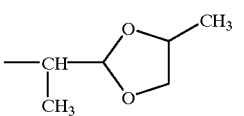 | |

-continued

| No. | R¹ | R² | R³ | R⁵ | R⁶ | Freeze pt. [° C.] or $n_D$ (° C.) |
|---|---|---|---|---|---|---|
| 78 | CH₃ | OCHF₂ | Br | NO₂ | —CH₂—CH₂—(1,3-dioxolan-2-yl) | |
| 78 | CH₃ | OCHF₂ | Br | NO₂ | —CHO | |
| 80 | CH₃ | OCHF₂ | Br | NO₂ | —CH=NOCH₃ | |
| 81 | CH₃ | OCHF₂ | Cl | NO₂ | —COO—CH(CH₃)₂ | |
| 82 | —(CH₂)₄— | | Cl | NO₂ | —COOC₂H₅ | |
| 83 | —(CH₂)₄— | | Cl | NO₂ | 4-methyl-1,3-dioxolan-2-yl | |
| 84 | —(CH₂)₄— | | Cl | NO₂ | 1,3-dioxolan-2-yl | |
| 85 | —(CH₂)₄— | | Cl | NO₂ | 1,3-dioxan-2-yl | |
| 86 | —(CH₂)₄— | | Cl | NO₂ | 5-methyl-1,3-dioxan-2-yl | |
| 87 | —(CH₂)₄— | | Cl | NO₂ | 5,5-dimethyl-1,3-dioxan-2-yl | |
| 88 | —(CH₂)₄— | | Br | NO₂ | —CH₂—(1,3-dioxan-2-yl) | |
| 89 | —(CH₂)₄— | | Br | NO₂ | —CH₂—CH₂—(1,3-dioxolan-2-yl) | |
| 90 | CH₃ | OCHF₂ | Cl | CN | —CH=N—OCH₂CCOH | 178 |
| 91 | CH₃ | OCHF₂ | Cl | CN | 5,5-dimethyl-1,3-dioxan-2-yl | |
| 92 | CH₃ | OCHF₂ | Cl | CN | 4,5-dimethyl-1,3-dioxolan-2-yl | viscous oil |

-continued

| No. | R¹ | R² | R³ | R⁵ | R⁶ | Freeze pt. [° C.] or $n_D$ (° C.) |
|---|---|---|---|---|---|---|
| 93 | CH₃ | OCHF₂ | Cl | CN | 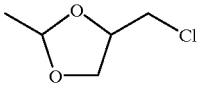 | 87 |
| 94 | CH₃ | OCHF₂ | Cl | CN | —CO₂C₂H₅ | 70 |
| 95 | CH₃ | OCHF₂ | Cl | CN | —CH=N—OCH₂CO₂CH₃ | 85 |
| 96 | CH₃ | OCHF₂ | Cl | CN | —CH=N—OCH₂CO₂C₂H₅ | 89 |
| 97 | CH₃ | OCHF₂ | Cl | NO₂ | —CHO | 75–76 |
| 98 | CH₃ | OCHF₂ | Cl | CN | 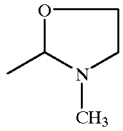 | 1.529 (20.2) |
| 99 | CH₃ | OCHF₂ | Br | CN | —CH=N—OCH₃ | 88–89 |
| 100 | CH₃ | OCHF₂ | Br | CN | 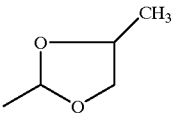 | 1.529 (20.2) |
| 101 | CH₃ | OCHF₂ | Cl | NO₂ | —CH=N—OCH₂CO₂C₂H₅ | 85 |
| 102 | CH₃ | OCHF₂ | Br | CN | —CH=N—OCH₂CO₂CH₃ | 108 |
| 103 | CH₃ | OCHF₂ | Br | CN | —CH=N—OCH₂CO₂-i-C₃H₇ | 102 |
| 104 | CH₃ | OCHF₂ | Br | CN | —CH=N—OCH₂CO₂CH₂CF₃ | 63 |
| 105 | CH₃ | OCHF₂ | Br | CN | —CH=N—OCH₂CO₂C₂H₄OCH₃ | 77 |
| 106 | CH₃ | OCHF₂ | Br | CN | —COOH | 180 |
| 107 | CH₃ | OCHF₂ | Br | CN | —CO₂C₂H₄OCH₃ | 1.5182 (24.0) |
| 108 | CH₃ | OCHF₂ | Br | CN | —CO₂CH₂CO₂CH₃ | |
| 109 | CH₃ | OCHF₂ | Cl | CN | —CO₂C₂H₄OCH₃ | |
| 110 | CH₃ | OCHF₂ | Cl | CN | —CO₂CH₂CF₃ | |
| 111 | CH₃ | OCHF₂ | Cl | CN | —CO₂CH₂CO₂CH₃ | |
| 112 | CH₃ | OCHF₂ | Cl | CN | 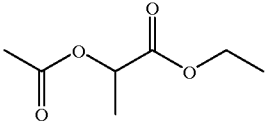 | |
| 113 | CH₃ | OCHF₂ | Cl | CN | 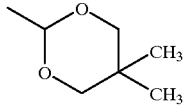 | |
| 114 | CH₃ | OCHF₂ | Cl | CN | 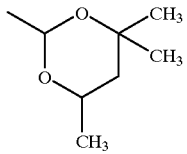 | 1.521 (24) |
| 115 | CH₃ | OCHF₂ | Br | CN | —CO₂CH₃ | |
| 116 | CH₃ | OCHF₂ | Cl | CN | —CO₂-i-C₃H₇ | 92–94 |
| 117 | CH₃ | OCHF₂ | Cl | CN | 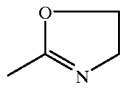 | |
| 118 | CH₃ | OCHF₂ | Cl | CN | 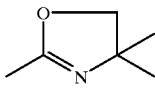 | |

-continued

| No. | R¹ | R² | R³ | R⁵ | R⁶ | Freeze pt. [° C.] or $n_D$ (° C.) |
|---|---|---|---|---|---|---|
| 119 | CH₃ | OCHF₂ | Cl | CN | (2-methyl-5,6-dihydro-4H-1,3-oxazine) | |
| 120 | CH₃ | OCHF₂ | Cl | CN | (2-methyl-4,4-dimethyl-5,6-dihydro-4H-1,3-oxazine) | |
| 121 | CH₃ | OCHF₂ | Cl | CN | (2,2-dimethyl-1,3-dioxane) | |
| 122 | CH₃ | OCHF₂ | Cl | CN | (2,2,4-trimethyl-1,3-dioxolane) | |
| 123 | CH₃ | OCHF₂ | Cl | CN | —CO—CH₃ | |

The following Examples explain the invention:

| Bayer - Code | |
|---|---|
| ALOMY | *Alopecurus myosuroides* |
| AGRRE | *Elymus repens* |
| AVEFA | *Avena fatua* |
| BROTE | *Bromus tectorum* |
| SETVI | *Setaria viridis* |
| PANSS | *Panicum sp.* |
| SORHA | *Sorghum halepense* |
| CYPES | *Cyperus esculentus* |
| ABUTH | *Abutilon theophrasti* |
| IPOSS | *Ipomoea purpurea* |
| GALAP | *Galium aparine* |
| MATCH | *Matricaria chamomilla* |
| POLSS | *Polygonum sp.* |
| SEBEX | *Sesbania exaltata* |
| SOLSS | *Solanum sp.* |
| VERPE | *Veronica persica* |
| VIOSS | *Viola sp.* |

0 = No damage
1 = 1–24% damage
2 = 25–74% damage
3 = 75–89% damage
4 = 90–100% damage

Example of Application

The indicated plant species in the greenhouse were treated after germination with the indicated compounds in application amounts of 0.1 kg active agent/ha. For this purpose, the compounds were used as an emulsion with 500 litre water/ha and were sprayed uniformly over the plants. 2 weeks after treatment, the compounds according to the invention showed an outstanding action against weeds as is shown in the following Table.

| Compound Example No. | ALOMY | AGRRE | AVEFA | BROTE | SETVI | PANSS | SORHA | CYPES | ABUTH | GALAP | IPOSS | MATCH | POLSS | SEBEX | SOLSS | VERPE | VIOSS |
|---|---|---|---|---|---|---|---|---|---|---|---|---|---|---|---|---|---|
| 1 | — | — | — | — | 3 | 3 | — | — | 4 | — | 4 | 4 | 4 | 4 | 4 | 3 | 3 |
| 3 | 4 | 3 | 3 | — | 3 | 3 | 3 | 3 | 4 | 3 | 4 | 4 | 4 | 4 | 4 | 4 | 3 |
| 4 | 4 | 3 | 4 | 4 | 4 | 3 | 4 | 3 | 4 | 4 | 4 | 4 | 4 | 4 | 4 | 4 | 4 |
| 7 | — | — | — | — | 3 | 3 | — | — | 4 | — | 3 | 3 | 4 | 4 | 4 | 3 | 3 |
| 8 | 4 | 4 | 4 | 4 | 4 | 4 | 3 | 4 | 4 | 4 | 4 | 4 | 4 | 4 | 4 | 4 | 4 |
| 12 | 4 | 3 | 4 | 4 | 4 | 3 | 3 | 4 | 4 | 4 | 4 | 4 | 4 | 4 | 4 | 4 | 4 |
| 14 | 3 | — | — | 3 | 4 | 3 | — | 3 | 4 | 4 | 4 | 4 | 4 | 4 | 4 | 4 | 4 |
| 31 | 4 | 3 | 3 | 3 | 3 | — | — | 3 | 4 | — | 4 | 4 | 4 | 4 | 4 | 4 | 4 |
| 34 | 4 | — | 4 | 3 | 4 | 4 | 4 | — | 4 | 4 | 4 | 4 | 4 | 4 | 4 | 4 | 4 |
| 43 | — | 3 | — | — | 3 | 3 | 3 | — | 4 | — | 4 | 3 | 4 | 4 | 4 | 4 | 3 |
| 44 | 3 | — | — | — | 3 | 3 | 3 | — | 4 | — | 4 | 3 | 4 | 4 | 4 | 4 | 3 |
| 52 | 4 | — | 3 | 3 | 4 | 4 | 3 | 3 | 4 | 4 | 4 | 4 | 4 | 4 | 4 | 4 | 4 |
| 62 | 4 | — | 4 | 4 | 4 | 4 | 3 | 3 | 4 | 4 | 4 | 4 | 4 | 4 | 4 | 4 | 4 |
| 65 | 4 | — | 4 | 3 | 4 | 4 | 3 | 4 | 4 | 4 | 4 | 4 | 4 | 4 | 4 | 4 | 4 |

-continued

| Compound Example No. | ALO MYE | AGR ERE | AVE RFAE | BRO TVI S | SEA TVI S | SAO NSA | CYR PRS | AGB ULH | IAP ATS | MAO TCS H | PAO LSX | SEL BES | SOL RSE | VER OPS | VIO S |
|---|---|---|---|---|---|---|---|---|---|---|---|---|---|---|---|
| 91 | 4 | — | 4 | 4 | 4 | 4 | 4 | — | 4 | 4 | 4 | 4 | 4 | 4 | 4 | 4 |
| 92 | 4 | — | 4 | 3 | 4 | 4 | 3 | — | 4 | 4 | 4 | 4 | 4 | 4 | 4 | 4 |
| 93 | 4 | — | 4 | 3 | 4 | 4 | 4 | — | 4 | 4 | 4 | 4 | 4 | 4 | 4 | 4 |
| 95 | — | — | — | 3 | 4 | 4 | 3 | — | 3 | 4 | 4 | 4 | 4 | 4 | 4 | 4 |
| 96 | — | — | 3 | 3 | 4 | 4 | 3 | — | 4 | 4 | 4 | 4 | 4 | 3 | 4 | 4 |
| Untreated | 0 | 0 | 0 | 0 | 0 | 0 | 0 | 0 | 0 | 0 | 0 | 0 | 0 | 0 | 0 | 0 |

We claim:

1. Substituted pyrazol derivatives of the general formula (I)

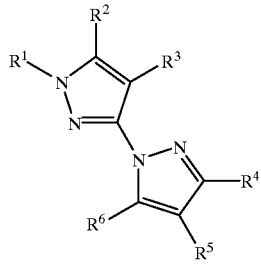

in which $R^1 = C_1-C_4$ alkyl, $R^2 = C_1-C_4$ alkyl, $C_1-C_4$- alkylthio, $C_1-C_4$ alkoxy; or $C_{1-C4}$ alkyl, $C_1-C_4$ alkylthio, $C_1-C_4$ alkoxy all substituted one or more times with halogen, $R^1$ and $R^2$ together form the group $—(CH_2)_m—$, $R^3$ = hydrogen or halogen, $R^4$ = hydrogen or $C_1-C_4$ alkyl, $R^5$ = hydrogen, nitro, cyano or the groups $—COOR^7$,

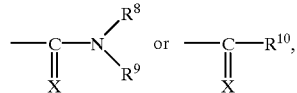

$R^6 =$

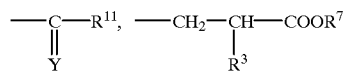

$R^7$, $R^8$ and $R^9$, independent of one another, are hydrogen or $C_1-C_4$ alkyl, $R^8$ and $R^9$, together with the adjacent nitrogen atom, form a 5-membered or 6-membered saturated heterocyclic ring, $R^{10}$ = hydrogen, $C_1-C_4$ alkyl, or a $C_1-C_4$ alkyl substituted one ore more times by halogen, $R^{11}$ = hydrogen, $C_1-C_6$ alkyl, $C_3-C_6$ cycloalkyl, $C_2-C_6$ alkenyl, $C_3-C_6$ alkynyl; or $C_1-C_6$ alkyl, $C_3-C_6$ cycloalkyl, $C_2-C_6$ alkenyl, $C_3-C_6$ alkynyl all substituted similarly or differently one or more times by halogen, hydroxy or $C_1-C_4$ alkoxy; or $C_2-C_8$ alkyl, $C_3-C_6$ cycloalkyl, $C_3-C_8$ alkenyl, $C_3-C_6$ alkynyl all interrupted times by oxygen; or the group $OR^{12}$, $R^{12} = C_1-C_6$ alkyl, $C_3-C_6$ cycloalkyl, $C_2-C_6$ alkenyl, $C_3-C_6$ alkynyl; $C_1-C_6$ alkyl substituted similarly or differently one or more times by halogen, hydroxy or by $C_1-C_4$ alkoxy Y = oxygen, sulphur, $—N—OR^{13}$ and

$R^{13}$ = hydrogen, $C_1-C_6$ alkyl, $C_3-C_6$ cycloalkyl, $C_2-C_6$ alkenyl, $C_3-C_6$ alkynyl; $C_1-C_6$ alkyl, $C_3-C_6$ cycloalkyl, $C_2-C_6$ alkenyl, $C_3-C_6$ alkynyl all substituted similarly differently one or more times by halogen, cyano, hydroxy or $C_1-C_4$ alkoxy; $C_2-C_8$ alkyl, $C_3-C_8$ cycloalkyl, $C_3-C_8$ alkenyl, $C_3-C_8$ alkynyl all interrupted one or more times by oxygen; $C_1-C_4$ alkoxycarbonyl-$C_1-C_4$ alkyl, which can optionally be substituted by halogen atoms; $C_1-C_4$ alkoxycarbonyl-$C_2-C_4$ alkenyl, which can optionally be substituted by halogen atoms; $C_1-C_4$ alkoxycarbonyl, $R^{14}$ and $R^{15}$, independent of one another, are hydrogen, halogen, cyano, carboxyl, formyl, $C_1-C_6$ alkyl, $C_3-C_6$ cycloalkyl, $C_2-C_6$ alkenyl, $C_3-C_6$ alkynyl; $C_1-C_6$ alkyl, $C_3C_6$ cycloalkyl, $C_2-C_6$ alkenyl, $C_3-C_6$ alkynyl all substituted similarly differently one or more times by halogen, cyano, hydroxy or $C_1-C_4$ alkoxy; $C_2-C_8$ alkyl, $C_3-C_8$ cycloalkyl, $C_3-C_8$ alkenyl, $C_3-C_8$ alkynyl all interrupted one times by oxygen; $C_1-C_4$ alkoxycarbonyl-$C_1-C_4$ alkyl, which can optionally be substituted by halogen atoms; $C_1-C_4$ alkoxycarbonyl-$C_2-C_4$ alkenyl, which can optionally be substituted by halogen atoms; $C_1-C_4$ alkoxycarbonyl, $C_1-C_4$ alkoxy or $C_1-C_4$ alkylthio, $R^{14}$ and $R^{15}$ together with the carbon atom form a saturated carbocyclic $C_3-C_6$ ring which can be interrupted one or more times by oxygen or sulphur, X = oxygen or sulphur.

2. Substituted pyrazol derivatives of the general formula (I) according to claim 1 in which R = methyl, $R^2$ = methylthio or difluormethoxy, $R^1$ and $R^2$ together form the group $—(CH_2)_4—$, $R^3$ = hydrogen, chlorine or bromine, $R^4$ = hydrogen, $R^5$ = hydrogen, nitro, cyano or the groups $—COOR^7$ or $—CXR_{10}$, $R^6=$

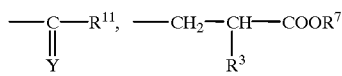

$R^7$ hydrogen or $C_1$–$C_4$ alkyl, $R^{10}$=hydrogen, $C_1$–$C_4$ alkyl, or a $C_1$–$C_4$ alkyl substituted one or more times by halogen, $R^{11}$=hydrogen, $C_1$–$C_6$ alkyl or the group —$OR^{12}$, $R^{12}$=hydrogen, $C_1$–$C_6$ alkyl, $C_3$–$C_6$ cycloalkyl, $C_2$–$C_6$ alkenyl, $C_3$–$C_6$ alkynyl; $C_1$–$C_6$ alkyl substituted similarly or differently one or more times by halogen, hydroxy, $C_1$–$C_4$ alkoxycarbonyl-$C_1$–$C_4$ alkyl or $C_1$–$C_4$ alkoxy, Y=oxygen, sulphur, —N—$OR^{13}$ and

$R^{13}$=hydrogen, $C_1$–$C_6$ alkyl, $C_3$–$C_6$ cycloalkyl, $C_2$–$C_6$ alkenyl, $C_3$–$C_6$ alkynyl; $C_2$–$C_8$-alkyl, $C_3$–$C_8$ cycloalkyl, $C_3$–$C_8$ alkenyl, $C_3$–$C_8$ alkynyl all interrupted on times by oxygen; $C_1$–$C_4$ alkoxycarbonyl-$C_1$–$C_4$ alkyl, which can optionally be substituted by halogen atoms; $C_1$–$C_4$ alkoxycarbonyl-$C_2$–$C_4$ alkenyl, which can optionally be substituted by halogen atoms; $C_1$–$C_4$ alkoxycarbonyl, $R^{14}$ and $R^{15}$, independent of one another, are hydrogen, halogen, cyano, carboxyl, formyl, $C_1$–$C_6$ alkyl, $C_3$–$C_6$ cycloalkyl, $C_2$–$C_6$ alkenyl, $C_3$–$C_6$ alkynyl; $C_1$–$C_4$ alkoxycarbonyl-$C_1$–$C_4$ alkyl, which can optionally be substituted by halogen atoms; $C_1$–$C_4$ alkoxycarbonyl, $C_1$–$C_4$ alkoxy or $C_1$–$C_4$ alkylthio, X=oxygen or sulphur.

3. Substituted pyrazol derivatives of the general formula (I) according to claim 1 in which $R^1$=methyl, $R^1$=difluormethoxy, $R^1$ and $R^2$ together form the group —$(CH_2)_4$—, $R^3$=chlorine, $R^4$=hydrogen, $R^5$=nitro or cyano, $R^6=$

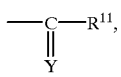

$R^{11}$=hydrogen or the group —$OR^{12}$, $R^{12}$=$C_1$–$C_6$ alkyl,

Y=oxygen, —N—$OR^{13}$ and

$R^{13}$=$C_1$–$C_6$ alkyl, $R^{14}$ and $R^{15}$, independent of one another, are hydrogen, halogen or $C_1$–$C_4$ alkoxy, X=oxygen.

4. A herbicidal composition which comprises an effective amount of at least one compound according to claim 1 and an inert carrier and/or auxiliary.

5. A method of combatting unwanted plant growth which comprises applying an effective amount of at least one compound according to claim 1 to said plants or to an environment where they reside.

6. The method according to claim 5, wherein the unwanted plants are monocotyledons.

7. The method according to claim 5, wherein the unwanted plants are dicotyledons.

* * * * *